United States Patent
Hamad et al.

(10) Patent No.: US 11,753,770 B2
(45) Date of Patent: Sep. 12, 2023

(54) CELLULOSE FILAMENT-STABILIZED PICKERING EMULSIONS

(71) Applicant: FPInnovations, Pointe-Claire (CA)

(72) Inventors: Wadood Yasser Hamad, Vancouver (CA); Chuanwei Miao, Richmond (CA)

(73) Assignee: FPInnovations, Pointe-Claire (CA)

( * ) Notice: Subject to any disclaimer, the term of this patent is extended or adjusted under 35 U.S.C. 154(b) by 198 days.

(21) Appl. No.: 16/307,380

(22) PCT Filed: Jun. 16, 2017

(86) PCT No.: PCT/CA2017/050736
§ 371 (c)(1),
(2) Date: Dec. 5, 2018

(87) PCT Pub. No.: WO2017/219127
PCT Pub. Date: Dec. 28, 2017

(65) Prior Publication Data
US 2019/0360151 A1    Nov. 28, 2019

Related U.S. Application Data

(60) Provisional application No. 62/352,079, filed on Jun. 20, 2016.

(51) Int. Cl.
*D21H 11/18*    (2006.01)
*D21C 9/00*    (2006.01)
*D21H 11/12*    (2006.01)

(52) U.S. Cl.
CPC ............. *D21H 11/18* (2013.01); *D21C 9/007* (2013.01); *D21H 11/12* (2013.01)

(58) Field of Classification Search
CPC ................................ D21C 9/007; D21H 11/12
See application file for complete search history.

(56) References Cited

U.S. PATENT DOCUMENTS 4,374,702 A * 2/1983 Turbak ..................... D01D 5/11
                                                           162/100
4,487,634 A * 12/1984 Turbak ................... A61K 8/027
                                                          106/163.01

(Continued)

FOREIGN PATENT DOCUMENTS

EP            1078008        8/2000
JP          2001002523        1/2001

(Continued)

OTHER PUBLICATIONS

Emulsions: Preparation and Stabilization, downloaded online Oct. 20, 2020, The Pharmaceuticals and Compounding Laboratory, downloaded from pharmlabs.unc.edu (Year: 2020).*

(Continued)

*Primary Examiner* — Anthony Calandra
(74) *Attorney, Agent, or Firm* — NORTON ROSE FULBRIGHT CANADA LLP

(57) ABSTRACT

The present disclosure is directed to a Pickering emulsion comprising cellulose filaments. The heterogeneity of the cellulose filament material is critical and beneficial to the formation of stable emulsions. Emulsions with high stability can be prepared by controlling the CF surface properties. It is provided an emulsion comprising an internal phase dispersed in a continuous external phase and cellulose filaments located at the interface of the internal phase and the external phase, wherein the emulsion comprises 50% in volume or more of the internal phase and a method of producing same.

18 Claims, 6 Drawing Sheets

[CF] = 2.4 %

[CF] = 1.2 %

[CF] = 0.6 %

Legend:

water

Oil phase

Cellulose Filaments (CF)

(56) References Cited

U.S. PATENT DOCUMENTS

| | | | |
|---|---|---|---|
| 6,534,071 B1 | 3/2003 | Tournilhac | |
| 9,328,211 B2 * | 5/2016 | Nemoto | C08B 15/04 |
| 10,364,297 B2 * | 7/2019 | Axrup | D21C 9/00 |
| 2013/0122071 A1 | 5/2013 | Cathala et al. | |

FOREIGN PATENT DOCUMENTS

| | | |
|---|---|---|
| JP | 2013534561 | 9/2013 |
| WO | 2010/058148 | 10/2010 |
| WO | 2010058148 | 5/2023 |

OTHER PUBLICATIONS

Soybean Oil, downloaded Oct. 20, 2020, Chemical Book, downloaded from www.chemicalbook.com (Year: 2020).*

Noureddini et al., Densities of Vegetable Oils and Fatty Acids, 1992, Papers in Biomaterials, 14. (Year: 1992).*

Pohler et al., Influence of fibrillation method on the chracter of nanofibrillated cellulose (NFC),2010, Tappi Internation Conference on Nanotechnology for the Forest Product Industry. (Year: 2010).*

Ougiya et al., "Emulsion-Stabilizing Effect of Bacterial Cellulose"; Bioscience, Biotechnology, and Biochemistry (1997), 61(9), p. 1541-1545.

Andresen et al., "Water-in-Oil Emulsions Stabilzed by Hydrophobized Microfibrillated Cellulose", Journal of Dispersion Science and Technology (2007), 28, p. 837-844.

Xhanari et al., "Emulsions Stabilized by Microfibrillated CEllulose: The Effect of Hydrophobization, Concentraton, and O/W Ratio", Journal of Dispersion Science and Technology (2011), 32, p. 447-452.

* cited by examiner

[CF] = 2.4 %   [CF] = 1.2 %   [CF] = 0.6 %

Legend:

water    Oil phase    Cellulose Filaments (CF)

CELLULOSE FILAMENT-STABILIZED PICKERING EMULSIONS

CROSS-REFERENCE TO RELATED APPLICATIONS

The present application is a U.S. National Phase of International Application No. PCT/CA2017/050736, filed on Jun. 16, 2017 and claiming priority from U.S. Provisional Application No. 62/352,079 filed Jun. 20, 2016, the content of which are hereby incorporated by reference in their entirety.

TECHNICAL FIELD

The present disclosure is directed to a Pickering emulsion comprising cellulose filaments.

BACKGROUND

A Pickering emulsion essentially consists of a two-phase emulsion that is stabilized by solid particles. When oil and water are mixed, in order to avoid collapse of the formed droplets of oil, solid particles are needed. The solid particles bind to the interface between the oil and water and stabilize the droplets. The emulsion can also contain water droplets stabilized in oil.

Cellulosic materials are known to be used as solid particles to stabilize Pickering emulsions. The effect of the morphology of cellulosic materials on the formation of Pickering emulsions has been studied for cellulose nanocrystals (CNC) or nanofibrils (CNF). Kalashnikova et al. (2013, Soft Matter, 9: 952-959) prepared oil-in-water (o/w) emulsions using cellulose nanocrystals derived from different sources with aspect ratios ranging from 13 to 160, and explored the stabilizing effects of unsulfated CNC. The electrostatic repulsion between the negatively charged sulfate groups on the surfaces of CNC has been shown to affect the stability of emulsions, and the ionic strength of the aqueous phase typically controls these interactions.

Xhanari et al. (2011, J. Colloid Interface Sci., 356: 58-62) used surface modified CNF to prepare water-in-oil (w/o) emulsions and investigated the effect of the structure of CNF at the water/oil interface. It was found that large entangled networks and small CNF aggregates did not stabilize the emulsion.

Winuprasith and Suphantharika (2013, Food Hydrocolloids, 32: 383-394) prepared microfibrillated cellulose (MFC) stabilized o/w emulsions and investigated the effect of MFC morphology and MFC concentration on the properties of the emulsions. It was concluded that the oil droplets were stabilized by the MFC fibrils adsorbed at the oil/water interface as well as the inter-droplet network and MFC network formed in the water phase. The same stabilization mechanism was also observed in bacterial cellulose stabilized emulsions owing to a similar entangled network structure within bacterial cellulose.

All of the known work, and research to-date involving cellulosic materials stabilized emulsions only examined low-internal phase systems, where the dispersed phase is 50% or lower (by volume) in the emulsion.

High-internal phase emulsions (HIPEs) are emulsion systems containing an internal, or dispersed, phase volume fraction greater than 74%, which is the maximum volume ratio of monodispersed non-deformable spheres when packed at the most efficient manner. The emulsions with an internal phase of 50-74% are normally called medium-internal phase emulsions (MIPEs).

There is still a need to be provided with alternative methods for producing Pickering emulsions, particularly MIPEs and/or HIPEs Pickering emulsions.

SUMMARY

In accordance to an embodiment, it is provided an emulsion comprising an internal phase dispersed in a continuous external phase and cellulose filaments located at the interface of the internal phase and the external phase, wherein the emulsion comprises 50% in volume or more of the internal phase.

It is also provided a method of producing an emulsion comprising an internal phase dispersed in a continuous external phase, comprising the steps of incorporating cellulose filaments to a continuous external phase; and dispersing the internal phase in a continuous external phase forming the emulsion, wherein the emulsion comprises 50% in volume or more of the internal phase.

In an embodiment, the emulsion described herein comprises 74% or more in volume of the internal phase.

In another embodiment, the emulsion comprises between 50%-83% in volume or more of the internal phase.

In an additional embodiment, the emulsion comprises between 74%-83% in volume of the internal phase.

In a further embodiment, the internal phase is hydrophobic and the external phase is hydrophilic.

In another embodiment, the internal phase comprises oil and the external phase comprises water.

In a further embodiment, the internal phase is hydrophilic and the external phase is hydrophobic.

In an additional embodiment, the internal phase comprises water and the external phase comprises oil.

In another embodiment, the cellulose filaments concentration is below 5 wt %.

In an additional embodiment, the cellulose filaments concentration is between 0.1-5 wt %.

In an additional embodiment, the cellulose filaments concentration is between 0.5-1.5 wt %.

In another embodiment, the cellulose filaments are from bleached or unbleached cellulose pulp fibers.

In an additional embodiment, the cellulose pulp fibers are from softwood, hardwood, perennial fibers, recycled fibres, or a combination thereof.

In an additional embodiment, the perennial fibers are from bagasse, flax, kenaf, hemp or a combination thereof.

In a further embodiment, the cellulose pulp fibers are from northern bleached softwood, hardwood kraft fibers, bleached chemi-thermo-mechanical pulps, thermo-mechanical pulps, or unbleached pulps.

In another embodiment, the cellulose filaments are inhomogeneous in mass and dimension.

In a further embodiment, the surface properties of the cellulose filaments are adjusted by changing the pH of suspension.

In a supplemental embodiment, the surface properties of cellulose filaments are partially modified by grafting/absorbing hydrophobic molecules or introducing other functional groups via chemical reactions.

In an embodiment, the cellulose filaments are chemically modified to be hydrophobic before being incorporated in the external phase comprising hydrophobic liquid.

In a further embodiment, the cellulose filaments dispersed in water comprising a salt prior to be incorporated to the internal phase.

In a further embodiment, the salt is monovalent, divalent, or trivalent.

In an embodiment, the cellulose filaments derived from unbleached pulps possess more hydrophobic surfaces compared to those from bleached pulps.

In a further embodiment, the unbleached cellulose filaments disperse in water.

In an additional embodiment, the unbleached cellulose filaments stabilize hydrophobic internal phase in water.

In an embodiment, the surface properties of the unbleached cellulose filaments can be adjusted by changing the pH of the aqueous phase, in which the cellulose filaments are dispersed.

In a further embodiment, the pH of the aqueous phase is 10 or higher.

In an additional embodiment, the pH of the aqueous phase is 12 or higher.

In an additional embodiment, the unbleached cellulose filaments distribute more homogeneous at the interface of oil and water at higher pH.

In an embodiment, the emulsions stabilized with unbleached cellulose filaments at high pH are highly stable.

In an additional embodiment, the cellulose filaments are incorporated to the internal phase by homogenization at a mixing speed of 300 to 30 000 rpm.

BRIEF DESCRIPTION OF THE DRAWINGS

Reference will now be made to the accompanying drawings.

DETAILED DESCRIPTION

Figure 1:
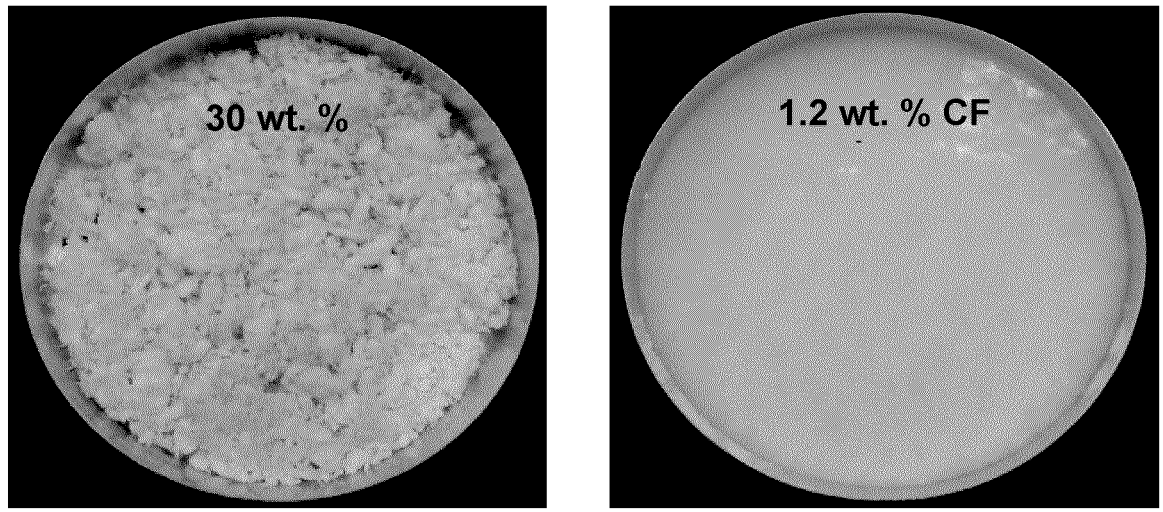
FIG. 1 illustrates the physical appearance of cellulose filament (CF) slurries at different consistencies: 30 wt. % wet CF (left), and 1.2 wt. % CF slurry after disintegration (right).

In accordance with the present disclosure, there is provided a Pickering emulsion comprising cellulose filaments. The emulsion described herein comprises an internal phase dispersed in a continuous external phase and cellulose filaments located at the interface of the internal phase and the external phase, wherein the emulsion comprises 50% in volume or more of the internal phase.

Disclosed herein are a method and system for preparing medium- and high-internal phase oil-in-water Pickering emulsions stabilized by a thin layer of controllably distributed cellulose filaments and whole or partial fibrous fragments of significantly larger dimensions. The fine fibrils surround the oil droplets without a high level of entanglement, and the emulsions exhibit viscous gel-like appearance. The total cellulose filament concentration encompassed herein is below 5 wt. %, otherwise the level of entanglement increases and the emulsions are de-stabilized. The inhomogeneity of the cellulose filament material is critical and beneficial to the formation of emulsions. The removal of large fragments to produce a homogeneous distribution of fibrillar mass or uniform physical dimensions, as in cellulose microfibrils or nanofibrils, leads to a higher level of entanglement and the lowering of the maximum oil content in the emulsion. This causes de-stabilization of the emulsion over time, and fails to produce high-internal phase Pickering emulsions.

The distribution of the fibrillar component and the whole, or partial, fibre fragments within the cellulose filament material are controlled by the magnitude of the mechanical energy applied to produce cellulose filaments. If the cellulose filaments are suitably rendered hydrophobic, they can be used to stabilize water-in-oil Pickering emulsions.

Contrary to Capron et al. (US 2014/0073706) which uses cellulose nanocrystals, which have a uniform distribution of size and charge, and are structurally and morphologically different from cellulose filaments as encompassed herein, it is provided the use of cellulose filamentous materials of controllably heterogeneous distribution of fibrillar material and fibrous segments, whole or partial, to stabilize medium- and high-internal phase Pickering emulsions. In particular, the cellulose filamentous materials, which are hydrophilic, can be used as-is in oil-in-water emulsions, or suitably modified by chemical means, for instance, to render them hydrophobic, and hence suitable for water-in-oil emulsions.

Cellulose filaments are typically, but not solely, obtained by applying mechanical forces (a combination of shearing, tensile and radial compressive forces) to native cellulose pulp fibres. The starting raw material can essentially be pure or a combination of lignocellulosic biomass, e.g., bleached or unbleached chemical, mechanical or chemi-mechanical wood pulp fibres. The native fibres can be softwood, hardwood, or perennial fibres, like bagasse, flax and kenaf. Perennial fibres, like bagasse, kenaf, flax or hemp can also be used as raw materials to produce CF. In certain cases, chemical or biochemical processing can additionally be applied to reduce the mechanical energy input and impart desirable attributes related to controlling fibrillation. It may thus be necessary to use selective chemical or enzymatic treatment to both, control the energy input and produce controllable distributions of heterogeneous physical components. The cellulose filaments thus produced necessarily possess a controlled combination of fine fibrils and some larger fibrous fragments. The quantity of large fragments is primarily related to the mechanical operating conditions. The ratio of the highly fibrillated component to fibrous fragments essentially influences the oil/water ratio and the total CF consistency in the water phase. Together, these factors can controllably tune the formation of medium- or high-internal phase emulsions.

Since CF is produced mainly by mechanical means, the chemical composition of the starting raw materials will be retained and can influence the properties of the final CF. For example, the CF produced from unbleached kraft pulp contains lignin and the presence of lignin can affect the surface properties of CF fibrils, thereby changing the level of entanglement by interfering with the formation of hydrogen bonding among the fibrils. When applied to an emulsion, this type of CF would be easier to distribute at the oil/water interface leading to more stable emulsions. When the surface property of this type of CF is further changed by adjusting the pH of CF suspension, i.e., increase the pH to a level where the lignin becomes soluble in water, CF fibrils can be further disentangled to form a much more uniform network at the oil/water interface. As a results, the formed emulsions have smaller oil droplet size, more uniform size distribution, and high stability in centrifuge test. Besides the composition of the raw materials, the surface properties of CF fibrils can also be modified chemically by attaching hydrophobic molecules, e.g., paper sizing agents, or physically by absorption of hydrophobic molecules, e.g., surfactants. In this case, the change of surface property should be controlled to a level where the CF still disperse in water, yet the CF fibrils should be disentangled. The other ways to modify CF include introduction of new functional groups on fibril surfaces, e.g., carboxymethylation, esterification.

The physical dimensions of the cellulose filamentous materials cover a spectrum for the fibrillar material, which can have micron to nanometer widths, and varying lengths in the range of microns to millimetres. The fibre segments can typically be in the micron to submicron range. It is critical that both, fibrillar materials or elements are present, as well as whole or partial fibrous segments to function as efficient and effective stabilizers to these emulsions. Solely fibrillar or fibrous segments of uniform size will fail to stabilize the emulsions.

CF can be produced using various levels of refining energy ranging from several hundred to several thousand kWh/T. The level of refining energy imparts a specific level of fibrillation and generation of fibre fragments through either fibre cutting, fibre splitting or defibrillation. The raw material when subjected to refining mechanical action undergoes a combination of shear and tensile forces, as well as radial compressive forces. Selective chemical, enzymatic or combinations of both can be applied to lower the mechanical energy input, on the one hand, but also to guide the level and manner of fibre development, i.e., the extent to which fibrillation can occur and fibre fragments generated.

The starting raw material for producing CF can be, for example, but not limited to, northern bleached softwood kraft (NBSK) pulp fibres. Subsequently, for the preparation of emulsions, CF can be used dry or in a slurry of any practical consistency (0.001-50 wt. %). When preparing the Pickering emulsions, the CF aqueous suspensions should ideally be at a specific concentration, such as for example 1.2 wt. %, following a simple disintegration and/or homogenization protocol.

To disperse CF in water, wet CF (containing, for instance, 24 g of dry weight) is mixed with 2 L of 90° C. hot deionized water (DI) water in a standard pulp disintegrator and beaten for 45,000 revolutions or 15 min. The resulting viscous CF slurry will have a consistency of 1.2 wt. % (FIG. 1). To get CF slurries with higher consistency, this 1.2% CF slurry can further be concentrated using, for example, Whatman #42 filter paper on a Buchner funnel with the assistance of low pressure from a water aspirator. The resulting concentrated CF slurry can then be homogenized using a standard mixing assembly on a homogenizer (Silverson L4RT-A) equipped with a general purpose disintegrating screen and an axial flow head for 30 sec at 10,000 rpm. The consistency of CF in the final slurry can be determined gravimetrically.

The range of suitable CF concentrations for preparing medium- or high-internal phase Pickering emulsions is limited to 0.1 to 5.0 wt. % in order to maximize stability of the resulting emulsion. FIG. 1 depicts the physical state of higher-solid contents CF, and the ideal low-solids content CF to be used for preparing emulsions. The consistency of the CF in the final slurry can be determined gravimetrically, and to avoid any potential surface charge interference, a small amount of monovalent salt, say 50 mM of NaCl, can be added to the CF slurry.

Figure 2:
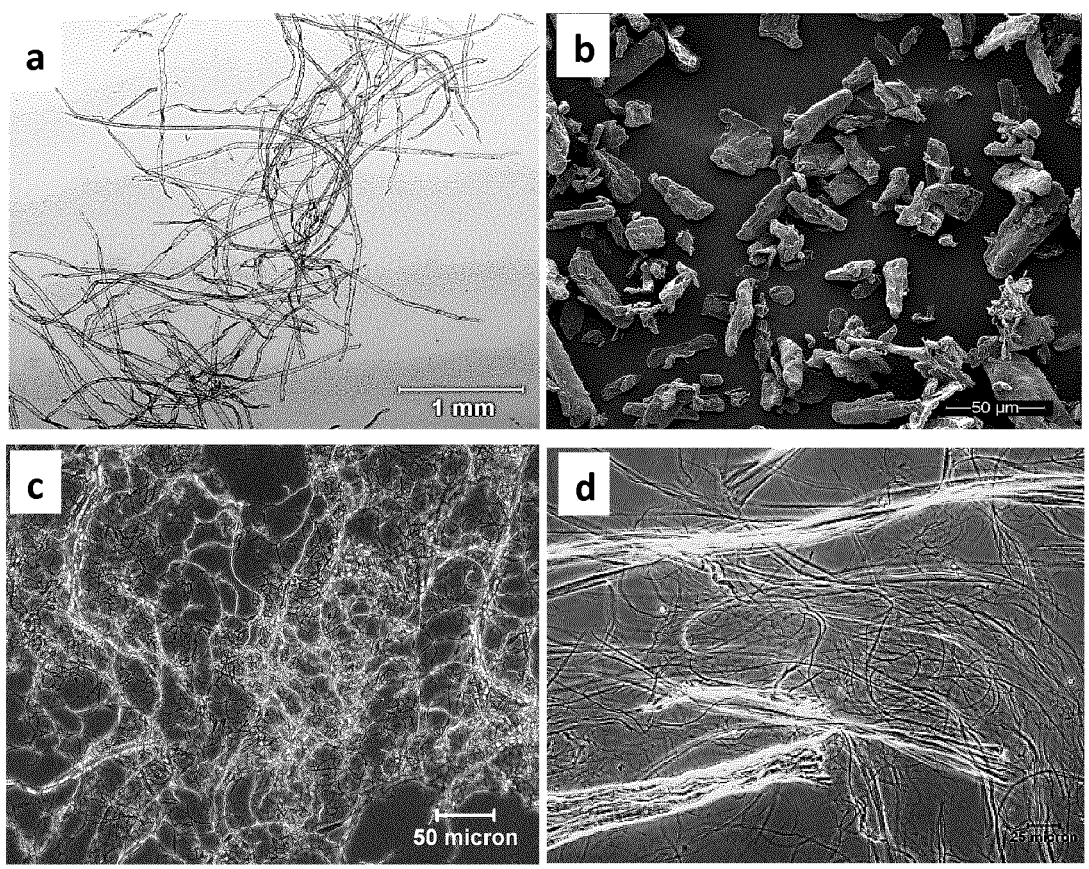
FIG. 2 illustrates a comparison of the morphology of raw materials used to produce emulsions, wherein northern bleached softwood kraft (NBSK) pulp fibres are shown in FIG. 2A; microcrystalline cellulose (MCC) particles, obtained via chemical means in FIG. 2B; cellulose nanofibrils (CNF) produced from bleached kraft pulp through mechanical means in FIG. 2C; and CF produced from NBSK by mechanical means as disclosed herein are shown in FIG. 2D.

FIG. 2 illustrates the typical morphology of the mechanically produced CF, the subject of the present disclosure, in relation to CNF, a type of cellulose fibrils processed using a combination of mechanical as well as chemical and/or enzymatic treatments leading to a highly homogeneous material relative to CF. CF is also compared to two distinctly different cellulose-based materials, wood pulp fibres (the starting raw material) and chemically-produced microcrystalline cellulose (MCC) particles.

To create the most efficient and effective system, it is disclosed the preparation of CF-stabilized Pickering emulsions via a two-step homogenization process using, for instance, a 1" tubular mixing assembly equipped with a general purpose disintegrating head on a homogenizer (Silverson L4RT-A). In the first step, a low amount of homogenization energy, between 300 and 2000 rpm, is applied for a short interval, ≤1 min. At this stage, the mixing head is lowered to the bottom of the vessel, or beaker, and only a portion of the oil phase is allowed to mix with the CF aqueous suspension. The second step entails rapidly increasing the mixing speed to 10,000 rpm (or higher, if necessary, but likely not to exceed 30,000 rpm). During the second step, this level of energy input is ideally maintained for an additional one minute, but not longer than 10 min. Variations on this approach are, however, possible and will lead to similar results.

Figure 3:
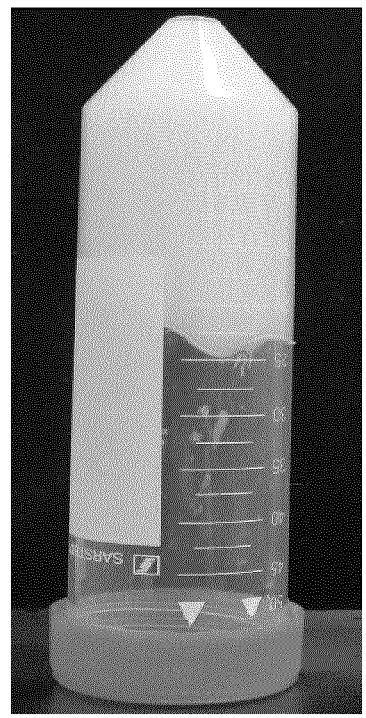
FIG. 3 illustrates the gel-like appearance of CF-stabilized high-internal phase Pickering emulsions. This specific example represents an emulsion composition of 78 vol. % mineral oil and 1.2 wt. % CF in the aqueous phase in accordance with one embodiment.
Figure 4:
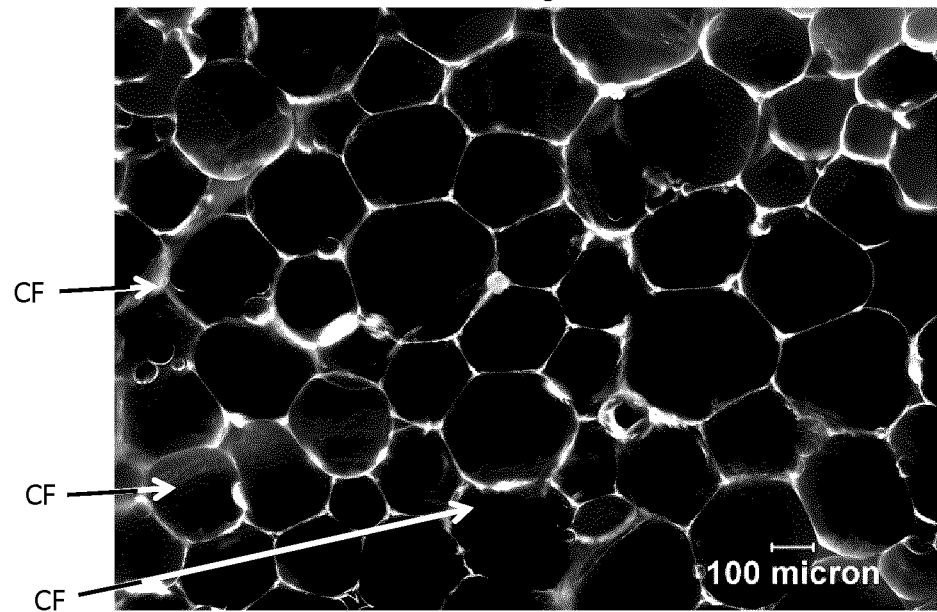
FIG. 4 illustrates the optical microscopy image of a typical CF-stabilized oil-in-water (o/w) Pickering emulsion. This specific example represents a sample whose CF concentration in the aqueous suspension=1.2 wt. % and oil content=78 vol. % in accordance with one embodiment. The image was taken under dark field mode using stack-focusing technique, whereby a series of images focusing on different layers of the emulsion sample are taken and combined to one picture using suitable imaging software. In the image, the cellulose filaments (CF) appear bright and the liquid phase dark.

Following the second homogenization step, the mixture instantaneously forms a gel-like emulsion (FIG. 3). The morphology of a typical CF-stabilized high-internal phase Pickering emulsion prepared according to the method and systems disclosed herein is illustrated in FIG. 4. The optical micrograph clearly shows each of the individual oil droplets being surrounded by a thin layer of cellulose filaments, thus preventing the oil droplets from coalescing. The oil droplets, depending on the specific requirements for producing a desired emulsion, can have a size distribution over a wide range from tens of microns to hundreds of microns. The oil droplets, in all cases, possess a compact structure with preferential polygonal shapes. Both the fibrils and large fragments of CF are clearly visible in the image shown in FIG. 4, thereby confirming the underlying mechanism of the disclosed approach that both fibrillar and fibre fragments are needed to ensure stability of the emulsion, i.e., a controlled distribution of the fibrillated material at the micron or sub-micron scale and fibre fragments at the millimeter scale.

Figure 5:
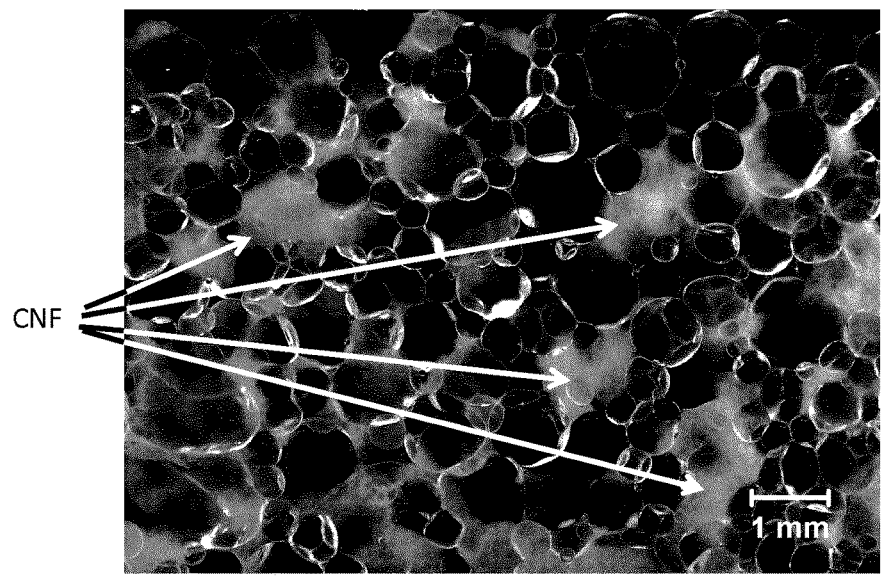
FIG. 5 illustrates an optical microscopy image of an oil-in-water (o/w) emulsion stabilized with cellulose nanofibrils (CNF) in accordance with one embodiment. CNFs are produced via a combination of mechanical and chemical or enzymatic treatment from bleached kraft pulp to result in highly fibrillated cellulose material. CNF is homogeneous without large fragments. The CNF concentration in the aqueous suspension=1.2 wt. % and oil content=80 vol. %. The image was taken using dark field mode at low magnification, and the white cloudy material is entangled CNF fibrils.

The cellulose filaments (CF) encompassed herein are heterogeneous systems consisting of fine fibrils and large fragments (FIG. 2C). The presence of large fragments can prevent the entanglement of fine fibrils in two particular ways. The fibre fragments can controllably and selectively infiltrate the fibrillar network, and thus prevent the fibrillar network from being entangled. In addition, the fibre fragments can effectively reduce the quantity of fine fibrils at the same mass consistency, thereby controllably creating a heterogeneous distribution of fibrillar mass and fibre fragments. Since the entanglement level of CF fibrils plays an important role in influencing the formation, and subsequent stability, of the emulsions, it was of relevance to investigate a system without the large fragments, i.e., a more homogeneous distribution of fibrillar mass, unlike the CF material being described in this disclosure. For this purpose, a cellulose nanofibrils (CNF) sample produced from bleached softwood kraft pulp, a similar raw material as CF's, is used to compare with CF. At similar concentration of cellulose materials and oil content, the emulsion containing CNF shows different appearance and is unstable. This discrepancy is clearly revealed by FIG. 5. It is apparent from FIG. 5 that the highly entangled CNF fibrils cannot disentangle and distribute at the oil/water interface. Rather, the majority of the CNFs exist in the system as entangled blobs (the white clouds in FIG. 5), and the dimensions of oil droplets in the CNF-stabilized emulsion become very large due to lack of stabilizing materials.

Accordingly, it is not the chemical composition per se, but the geometry and morphology that are key factors to stabilizing Pickering emulsions. For instance, CF-stabilized Pickering emulsions can be contrasted with those prepared using northern bleached softwood kraft (NBSK) fibres or microcrystalline cellulose (MCC), both commonly used in a variety of emulsion systems. NBSK pulp fibres, a typical raw material for producing CF, consist of discrete fibres whose widths fall in the range 20-40 μm and lengths 2-3 mm (FIG. 2A). MCC, on the other hand, is composed of discrete particulates with irregular shapes whose average size is approximately 20 μm (FIG. 2B).

Figure 6:
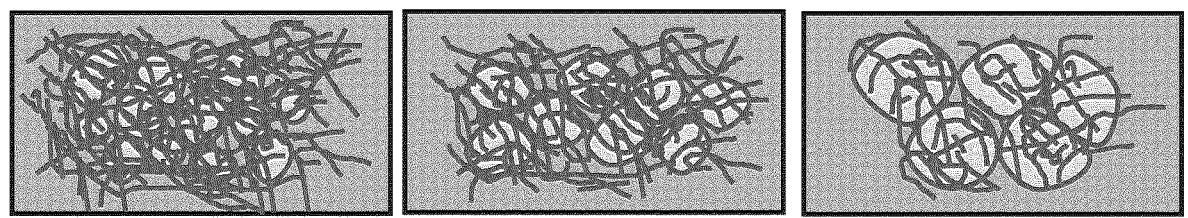
FIG. 6 illustrates a schematic representation of the stabilization mechanism of CF based o/w Pickering emulsions at different CF consistencies in water.

The entanglement of fine fibrils de-stabilizes emulsions and prevents increasing the oil content to reach the level of high-internal phase Pickering emulsions. The unique mechanism responsible for stabilizing both medium- and high-internal phase Pickering emulsions using CF, where there is a heterogeneous distribution of fibrillar mass and fibre fragments, is explained in FIG. 6. In this mechanism, the properties of the emulsions are primarily influenced by the level of entanglement of CF fibrils and infiltration of fibrous fragments, which is directly related to CF consistency in the aqueous phase. The homogenization processing used for preparing the Pickering emulsions is incapable of de-entangling the fibrillar networks. Hence, the oil droplets in the emulsion system can only stay in the free space or voids within the entangled network. These oil droplets will thus take the shape permitted by the specific geometry imparted by the specific distribution of fibrillar network, and may undergo some deformation. This is clearly evidenced by the wide range of size distribution and hexagonal geometry of the oil droplets within the high-internal phase Pickering emulsion presented in FIG. 4.

Figure 9:
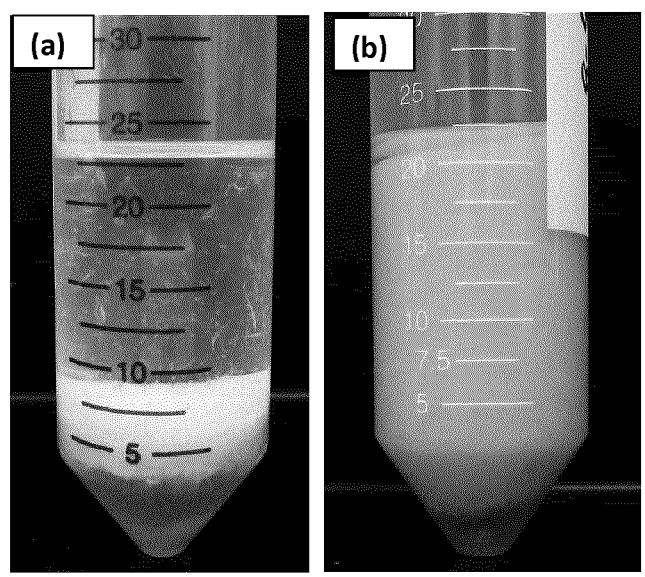
FIG. 9 illustrates the change in appearance for emulsions stabilized with unbleached CF at different pH. The pH values of the aqueous CF suspensions are 7 for (a) and 14 for (b). Both emulsions consist of 2.4 wt. % unbleached CF and 80 vol. % of oil. The images were taken after centrifuging the emulsions at 4,000 rpm for 10 min.

As an illustrative example, oil-in-water emulsions with 75 vol. % oil and 1.2% NBSK or MCC were prepared and their properties compared with those of the high-internal phase Pickering emulsions stabilized with 1.2% CF. Unlike the gel-like appearance of the CF-stabilized Pickering emulsion, both NBSK- and MCC-stabilized emulsions exhibit low viscosity and appear free to flow (see FIG. 7). Furthermore, the oil droplets in the NBSK or MCC emulsions are very large and directly visible in the photographs owing to the large dimension of the NBSK pulp fibres or MCC particles (FIG. 9), and the NBSK pulp or MCC particles appear precipitated at the bottom with a layer of water clearly separated in both cases. On the other hand, the CF-stabilized emulsion is unperturbed over a 30-day storage period. Indeed, it remains stable over storage, at ambient conditions, for over 12 months (and counting).

Figure 7:
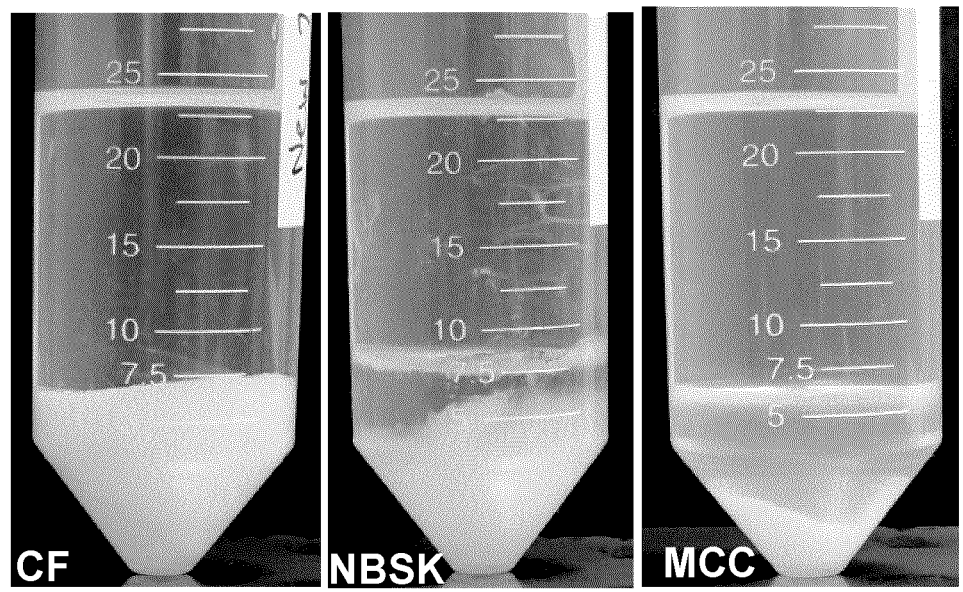
FIG. 7 illustrates the appearance of Pickering emulsions stabilized by CF, northern bleached softwood kraft (NBSK) pulp fibres and microcrystalline cellulose (MCC) after centrifugation at 4,000 rpm for 10 min. All emulsions consist of 1.2 wt. % stabilizing materials (CF, NBSK or MCC) in the aqueous phase and 75 vol. % of mineral oil. The CF-stabilized emulsion remains stable after centrifugation, unlike those stabilized by NBSK or MCC.
Figure 8:
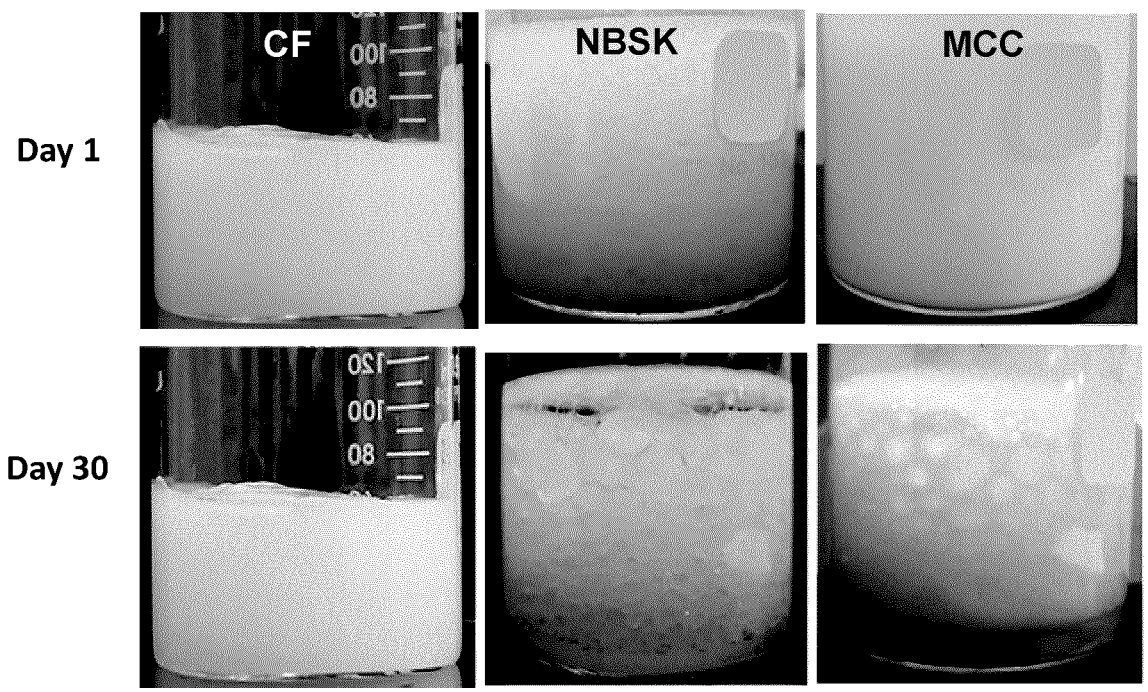
FIG. 8 illustrates the appearance of Pickering emulsions stabilized by CF, northern bleached softwood kraft (NBSK) pulp fibres and microcrystalline cellulose (MCC) depicting their stability over 30-day storage. All emulsions consist of 1.2 wt. % stabilizing materials (CF, NBSK or MCC) in the aqueous phase and 75 vol. % of mineral oil. The CF-stabilized emulsion remains stable after storage for 30 days at ambient conditions, unlike those stabilized by NBSK or MCC.
Figure 10:
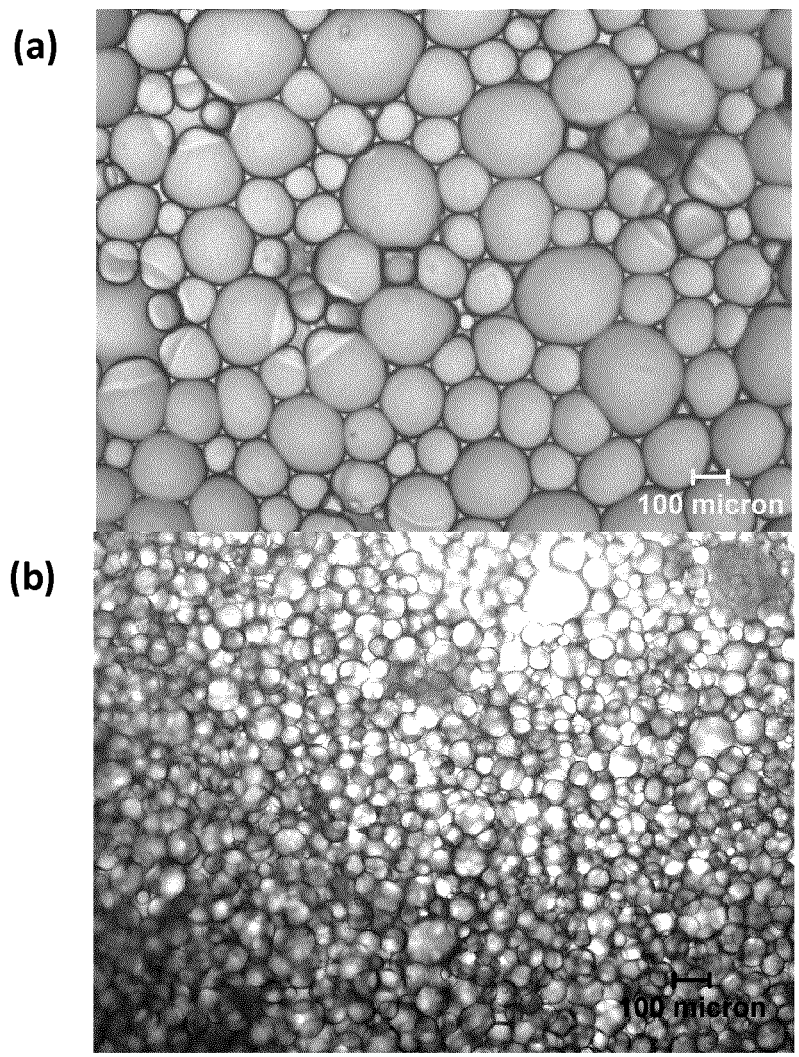
FIG. 10 illustrates optical microscopy images of oil-in-water emulsions stabilized with unbleached CF at different pH. Images (a) and (b) demonstrate the appearance of oil drops when the CF suspension is pH 7 and 14, respectively.

In another example, oil-in-water emulsions were prepared using CF produced from unbleached kraft pulp. At 2.4 wt. % CF concentration and 80 vol. % oil content, the emulsions demonstrated totally different stability in the centrifugation test when the CF suspension was at neutral and high pH. As shown in FIG. 7, owing to the high oil content, most of the neutral pH emulsion phase-separate after centrifuging at 4,000 rpm for 10 min. However, drastic change occurred by merely increasing the pH to 14, where most of the emulsion phase was retained after centrifugation at the same conditions. The optical microscopy images in FIG. 10 reveal the difference of oil droplets in these two emulsions. At neutral pH, the oil droplets are large polygonal shaped with a wide size distribution, which is similar to the emulsion stabilized with CF produced from NBSK pulp (see FIG. 4). At high pH, however, the oil droplets become much smaller and more uniform.

The Pickering emulsions prepared according to the method and system disclosed herein have been shown to remain stable for longer than 12 months, without any phase separation when kept in any standard container at ambient conditions. This excellent stability bodes very well for using CF as a suitable stabilizer for Pickering emulsions to be used in a wide variety of industries ranging from food, pharmaceutical preparations, paints and coatings to engineering systems used for a multitude of industrial applications (e.g., oil and gas drilling fluids).

While the disclosure has been described in connection with specific embodiments thereof, it will be understood that it is capable of further modifications and this application is intended to cover any variations, uses, or adaptations, including such departures from the present disclosure as come within known or customary practice within the art, and as may be applied to the essential features hereinbefore set forth, and as follows in the scope of the appended claims.

What is claimed is:

1. An emulsion comprising an internal phase dispersed in a continuous external phase and cellulose filaments located at the interface of the internal phase and the external phase, wherein the emulsion comprises 50% in volume or more of the internal phase at 25° C., wherein the cellulose filaments are heterogeneous in mass and dimension consisting of fine fibrils ranging from 44 microns to 70 microns in length and 30-100 nanometers in width, and large fragments ranging from 496 microns to 3520 microns in length and 9-23 microns in width.

2. The emulsion of claim 1, wherein said emulsion comprises 74% or more in volume of the internal phase.

3. The emulsion of claim 1, wherein said emulsion comprises between 50%-83% in volume or more of the internal phase.

4. The emulsion of claim 1, wherein said emulsion comprises between 74%-83% in volume of the internal phase.

5. The emulsion of claim 1, wherein the internal phase is hydrophobic and the external phase is hydrophilic.

6. The emulsion of claim 5, wherein the internal phase comprises oil and the external phase comprises water.

7. The emulsion of claim 1, wherein the internal phase is hydrophilic and the external phase is hydrophobic.

8. The emulsion of claim 7, wherein the internal phase comprises water and the external phase comprises oil.

9. The emulsion of claim 1, wherein the cellulose filaments concentration is below 5 wt %.

10. The emulsion of claim 1, wherein the cellulose filaments concentration is between 0.1-5 wt %.

11. The emulsion of claim 1, wherein the cellulose filaments concentration is between 0.5-1.5 wt %.

12. The emulsion of claim 1, wherein the cellulose filaments are from bleached or unbleached cellulose pulp fibers.

13. The emulsion of claim 12, wherein the cellulose pulp fibers are from softwood, hardwood, perennial fibers, recycled fibres, or a combination thereof.

14. The emulsion of claim 13, wherein the perennial fibers are from bagasse, flax, kenaf, hemp or a combination thereof.

15. The emulsion of claim 12, wherein the cellulose pulp fibers are from northern bleached softwood, hardwood kraft fibers, bleached chemi-thermo-mechanical pulps, thermo-mechanical pulps, or unbleached pulps.

16. The emulsion of claim 1, wherein the surface properties of cellulose filaments comprises hydrophobic molecules or other functional groups.

17. A method of producing an emulsion as defined in claim 1, comprising the steps of:
    a) incorporating cellulose filaments to an external phase; and
    b) dispersing the internal phase in a continuous external phase forming the emulsion, wherein the emulsion comprises 50% in volume or more of the internal phase.

18. The method of claim 17, wherein the cellulose filaments are dispersed in water comprising a salt prior to be incorporated to the internal phase.

* * * * *